US012788699B2

(12) United States Patent
Choi et al.

(10) Patent No.: US 12,788,699 B2
(45) Date of Patent: Nov. 10, 2026

(54) METHOD FOR PREPARING LOW-MOLECULAR-WEIGHT SILK SERICIN, AND COSMETIC COMPOSITION COMPRISING SERICIN PREPARED THEREBY

(71) Applicants: Yoon Chul Choi, Jinju-si (KR); HEWON CO., LTD., Jinju-si (KR)

(72) Inventors: Yoon Chul Choi, Jinju-si (KR); Kang Min Choi, Jinju-si (KR); Mi Eun Lee, Jinju-si (KR); Young Moo Choo, Jinju-si (KR); Tak Ko, Jinju-si (KR)

(73) Assignees: Yoon Chul Choi, Jinju-si (KR); HEWON CO., LTD., Jinju-si (KR)

( * ) Notice: Subject to any disclaimer, the term of this patent is extended or adjusted under 35 U.S.C. 154(b) by 521 days.

(21) Appl. No.: 18/275,257

(22) PCT Filed: Jun. 14, 2022

(86) PCT No.: PCT/KR2022/008353

§ 371 (c)(1),
(2) Date: Jan. 12, 2024

(87) PCT Pub. No.: WO2022/265335

PCT Pub. Date: Dec. 22, 2022

(65) Prior Publication Data

US 2025/0319012 A1 Oct. 16, 2025

(30) Foreign Application Priority Data

Jun. 15, 2021 (KR) ........................ 10-2021-0077563

(51) Int. Cl.
*A61K 8/64* (2006.01)
*A61Q 19/00* (2006.01)
(Continued)

(52) U.S. Cl.
CPC ................ *A61K 8/64* (2013.01); *A61Q 19/00* (2013.01); *C07K 1/14* (2013.01); *C07K 14/43586* (2013.01)

(58) Field of Classification Search
CPC . A61K 8/64; A61Q 19/00; C07K 1/14; C07K 14/43586
See application file for complete search history.

(56) References Cited

U.S. PATENT DOCUMENTS

2018/0344605 A1* 12/2018 Diaz Gomez ........ A61K 8/4973

FOREIGN PATENT DOCUMENTS

| | | |
|---|---|---|
| JP | 4-202435 A | 7/1992 |
| JP | 7-67686 A | 3/1995 |

(Continued)

OTHER PUBLICATIONS

Rozanov et al., "Production of subtilisin proteases in bacterial yeast" in 063op/Review, Feb. 2021) (Year: 2021).*

(Continued)

*Primary Examiner* — Blessing M Fubara
(74) *Attorney, Agent, or Firm* — Birch, Stewart, Kolasch & Birch, LLP

(57) ABSTRACT

Low-molecular-weight sericin, according to the present disclosure, can enhance absorption efficiency when applied to the skin and, especially, has excellent antioxidant and tyrosinase inhibitory effects, and thus can fundamentally inhibit the degradation of elastin and collagen, which maintain skin elasticity. In addition, sericin has all essential amino acids except for tryptophan and thus can even be effectively used in wound dressings or food, in addition to cosmetic products.

13 Claims, 12 Drawing Sheets

(51) Int. Cl.
*C07K 1/14* (2006.01)
*C07K 14/435* (2006.01)

(56) References Cited

FOREIGN PATENT DOCUMENTS

| | | | | | |
|---|---|---|---|---|---|
| JP | 2004066177 | | * | 3/2004 | |
| JP | 2008-289370 | A | | 12/2008 | |
| JP | 2008289370 | | * | 12/2008 | |
| JP | 5603857 | B2 | * | 10/2014 | .............. A61P 19/00 |
| KR | 10-1999-0086233 | A | | 12/1999 | |
| KR | 10-2010-0123514 | A | | 11/2010 | |
| KR | 10-2016-0062152 | A | | 6/2016 | |
| KR | 10-2017-0106955 | A | | 9/2017 | |
| KR | 20170105955 | A | * | 9/2017 | ............... A61K 8/64 |
| KR | 10-2018-0101802 | A | | 9/2018 | |
| KR | 10-2021-0153142 | A | | 12/2021 | |
| WO | WO 89/06279 | A1 | | 7/1989 | |
| WO | WO 92/19729 | A1 | | 11/1992 | |
| WO | WO 93/18140 | A1 | | 9/1993 | |
| WO | WO 98/20115 | A1 | | 5/1998 | |
| WO | WO 98/20116 | A1 | | 5/1998 | |
| WO | WO 98/34946 | A1 | | 8/1998 | |
| WO | WO 01/44452 | A1 | | 6/2001 | |
| WO | WO 01/58275 | A2 | | 8/2001 | |
| WO | WO 01/58276 | A2 | | 8/2001 | |
| WO | WO 03/006602 | A2 | | 1/2003 | |
| WO | WO 2004/099401 | A1 | | 11/2004 | |
| WO | WO 2011/036263 | A1 | | 3/2011 | |

OTHER PUBLICATIONS

International Search Repori (PCT/ISA/210) issued in PCT/KR2022/008353 mailed on Sep. 13, 2022.

Siezen et al., "Homology modelling and protein engineering strategy of subtilases, the family of subtilisin-like serine proteinases", Protein Engineering, 1991, vol. 4, No. 7, pp. 719-737.

Siezen et al., "Subtilases: The superfamily of subtilisin-like serine proteases", Protein Science (1997), vol. 6, pp. 501-523.

* cited by examiner

Tris-Glycine SDS-PAGE

Tris-Tricine SDS-PAGE

Tris-Glycine SDS-PAGE

Tris-Tricine SDS-PAGE

METHOD FOR PREPARING LOW-MOLECULAR-WEIGHT SILK SERICIN, AND COSMETIC COMPOSITION COMPRISING SERICIN PREPARED THEREBY

TECHNICAL FIELD

The present disclosure relates to a method for preparing a low-molecular-weight silk sericin and a cosmetic composition containing the sericin prepared therefrom. More particularly, the present disclosure relates to a method for preparing a low-molecular-weight silk sericin and a cosmetic composition containing the sericin prepared therefrom, which improves skin absorption, whitening, and antioxidant capacity by controlling degradation conditions during enzymatic degradation to obtain a low-molecular-weight sericin of 3 kDa or less.

BACKGROUND ART

The silk produced by a cocoon is a natural protein source of high purity and is composed of fibroin, which makes up the fibers, and sericin, the glue that wraps around fibroin and holds them together. Among them, sericin is dissolved when cocoons are immersed in hot water and has an amino acid composition similar to that of fibroin but has a low content of glycine, alanine, and tyrosine and has a high content of serine and acidic amino acids. The molecular weight of sericin obtained by the high-pressure scouring method is generally between 30,000 and 100,000, with a wide distribution of molecular weights.

Sericin, which accounts for about 30% of the weight of cocoon yarn, has been dissolved and discarded as an unnecessary component in the scouring process of silk fabrics. The main amino acids of sericin are composed of 33% serine, 17% glycine, 9% threonine, and 19% asparagine, and the like, resulting in rich hydrophilicity, excellent moisturizing properties, and biocompatibility, and therefore sericin is a natural material that is good for the skin. Therefore, sericin is increasingly used in textile products, basic cosmetics such as lotions, rinses, and creams, and skin care products such as eyelash makeup, atopic relief, and sun protection. Recently, new uses of sericin in the medical field, such as cell culture reagents and enzyme stabilizers, are expected to expand since sericin has been found to inhibit the activity of tyrosinase, prevent lipid peroxidation, promote cell proliferation, and stabilize oxygen.

However, since sericin has a very high molecular weight, sericin is prone to gelation in aqueous solution, and its solubility decreases significantly when freeze-dried, and for this reason, sericin has not been used industrially until now.

Therefore, in order to overcome these problems, lowering the molecular weight of sericin is essential. Until recently, the enzymatic hydrolysis method was known to be the most efficient method for lowering the molecular weight of sericin, in which enzymes are added directly to the silk protein solution to degrade the high molecular weight of sericin to a lower molecular weight. In general, the enzymatic hydrolysis method is recognized as superior to other methods in that the enzymatic hydrolysis method is environmentally friendly and cuts only at specific sites due to the reaction specificity of the enzyme.

However, it is difficult to isolate the sericin protein that is responsible for the actual physiological activity because the sericin is composed of a mixture of proteins rather than a single type, and when extracted, new proteins are formed due to further hydrolysis. Whereas, even after hydrolysis, the molecular weight of sericin is large, which limits its use.

DISCLOSURE

Technical Problem

The present disclosure was devised to solve the above problems. Specifically, an objective of the present disclosure is to provide a method for preparing a low-molecular-weight silk sericin and a cosmetic composition containing the sericin prepared therefrom, which improves skin absorption, whitening, and antioxidant capacity by controlling degradation conditions during enzymatic degradation to obtain a low-molecular-weight sericin of 3 kDa or less.

Technical Solution

The present disclosure relates to a method for preparing low-molecular-weight silk sericin and a cosmetic composition containing the sericin prepared therefrom.

One aspect of the present disclosure relates to a method of preparing a low-molecular-weight silk sericin, the method including:

a) scouring the silk yarn with a scouring solution to separate fibroin fibers and sericin; and b) mixing the separated sericin with an enzyme composition to prepare a low-molecular-weight sericin, in which the low-molecular-weight sericin has a molecular weight of 3 kDa or less.

In the present disclosure, step a) can be performed at 90° C. to 150° C. for 10 to 120 minutes, in which the scouring agent includes one or more alkaline agent selected from sodium carbonate, sodium bicarbonate, potassium carbonate, and sodium hydroxide; soap; one or more sulfates selected from sodium hyposulfite, calcium sulfate, and magnesium sulfate; and a solvent.

Furthermore, the enzyme composition may be a mixture of subtilisin or a derivative thereof and a solvent, in which the enzyme composition may have a concentration of 1% to 30% by weight and a pH in the range of 5 to 9%, and the step b) is performed at a temperature in the range of 30° C. to 70° C. for a time of 1 to 24 hours.

Another aspect of the present disclosure relates to a cosmetic composition containing sericin prepared according to the method of the present disclosure, in which the cosmetic composition may further include one or more essential oils selected from the group consisting of *Eucalyptus*, Peppermint, Grapefruit, Nenolri, Niaouli, Lavender, Lime, Lemon, Lemongrass, *Melissa officinalis*, Rosemary, Rosewood, Majoram, *Citrus madurensis*, Myrtle, Myrrh, Basil, *Verbena*, Birch, Bergamot, Bay, Benzoinum, Cypress, Sandalwood, and Cinnamon, Cedarwood, Citronella, Orange sweet, Ylang ylang, Jasmine, Geranium, Juniper berry, Ginger, Chamomile, Camphor, Clary sage, Thyme, Tangerine, Tea tree, Palmarosa, Patchouli, Petitgrain, Frankincense, Fennel, Hyssop, Green tea, Ginger, Chinese Liquorice, Schisandra, Coptis, Aloe vera, and Broccoli.

Advantageous Effects

Low-molecular-weight sericin, according to the present disclosure, can enhance absorption efficiency when applied to the skin and, especially, has excellent antioxidant effect and tyrosinase inhibitory effect, and thus can fundamentally inhibit the degradation of elastin and collagen, which maintain skin elasticity.

In addition, sericin has all essential amino acids except for tryptophan and thus can even be effectively used in wound dressings or food, in addition to cosmetic products.

DESCRIPTION OF DRAWINGS

FIGS. 7A and 7B show the molecular weight distribution of the sericin hydrolysates of the ALCALASE™ and flavourzyme of Example 5, in which FIG. 7A shows the molecular weight distribution on a Tris-Glycine SDS-PAGE, and FIG. 7B shows the molecular weight distribution on a Tris-Tricine SDS-PAGE; and FIGS. 8A and 8B show the molecular weight distribution of the sericin hydrolysates of the ALCALASE™ and flavorzyme of Example 6, in which FIG. 8A shows the molecular weight distribution on a Tris-Glycine SDS-PAGE, and FIG. 8B shows the molecular weight distribution on a Tris-Tricine SDS-PAGE.

MODE FOR INVENTION

Figure 1A:
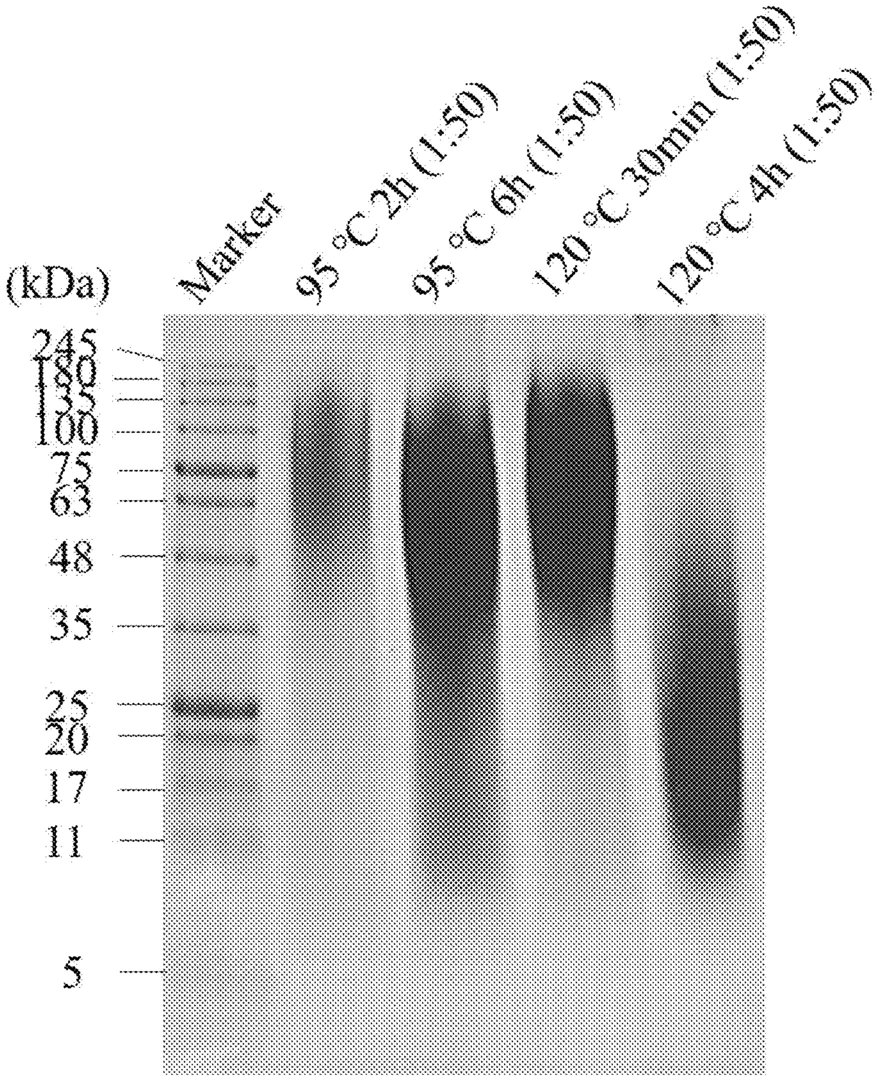
FIGS. 1A and 1B show the molecular weight distribution of the scoured sericin prepared through Preparation Example 1.

Hereinafter, a method of preparing low-molecular-weight silk sericin according to the present disclosure and a cosmetic composition containing sericin prepared therefrom will be described in detail with reference to embodiments and comparative examples. The following specific examples are provided as an example so that the idea of the present disclosure may be sufficiently transmitted to those skilled in the art.

Therefore, the present disclosure is not limited to the embodiments presented below and may be embodied in other forms, and the embodiments presented below are only described to clarify the spirit of the present disclosure, and the present disclosure is not limited thereto.

In this case, if there is no other definition of the technical terms and scientific terms used, it has the meaning normally understood by those with ordinary knowledge in the technical field to which the disclosure belongs, and the description of the known function and configuration that may unnecessarily obscure the gist of the disclosure is omitted in the following description.

In this disclosure, the term "silk yarn" refers to the raw silk produced by silkworms, insects belonging to the phylum Insectada, the order lepidoptera, the family Bombyxidae, the genus *Bombyx*, and the order MORI, and more specifically to the scoured silk obtained by a certain degree of scouring, mainly from which most impurities and some sericin have been removed.

A method for preparing a low-molecular-weight silk sericin, according to the present disclosure, the method including: a) separating fibroin fibers and sericin by scouring the silk yarn with a scouring solution; and b) preparing a low-molecular-weight sericin by mixing the separated sericin with an enzyme composition.

In general, natural fibers such as silk, cotton, and wool contain impurities in addition to fiber components. These impurities need to be removed before dyeing and processing, and in particular, degumming of silk fibers removes sericin from the fibers and removes so-called primary impurities such as waxes, fatty acid pigments, and inorganic substances, and secondary impurities such as emulsifiers and sizing agents used for twisting and weaving.

Silk fiber, also known as silk, is a so-called bicomponent fiber composed of fibroin, which accounts for about 75% of the total weight of the raw fiber, and sericin (silk glue), which accounts for about 25%, and fibroin has a high level of microstructure, which is composed of microfibril and fibril stages. Fibroin, a poorly soluble fibrous protein, serves as a fiber, while sericin, a soluble non-fibrous protein, protects the fibroin inside and connects the individual fibers.

Raw silk, which retains sericin, a protein that is relatively soluble in water, exhibits a somewhat stiff and rough texture, so raw silk is used in organza fabric, but sericin is a non-fibrillar protein that is not dense in structure and is weak to external impacts such as washing, sweating, and friction, so there are many problems in use. Therefore, this sericin is usually removed by a scouring process, and only the fibroin is processed into fibers for use.

In the present disclosure, the silk yarn is also called raw silk, which is fibered by applying a certain degree of scouring to the cocoon, meaning that the sericin is not completely removed from the cocoon, but some remain. Since the silk yarn as described above is not fully matured by scouring, the silk yarn has a somewhat thick, stiff, and cool texture similar to ramie due to the remaining sericin.

The silk yarn as described above has several advantages compared to the case of extracting sericin by directly scouring silkworm cocoons. First, cocoons often contain other amino acids or impurities besides sericin, but these impurities are removed during the process of scouring the cocoon to produce silk yarn so that only pure sericin can be obtained. In addition, the process of swelling and dissolution of the whole sericin in the scouring solution is completed before the elution of the whole sericin occurs, so that the residual sericin is unstably and unevenly retained in the fibroin, and since some hydrolysis of sericin has occurred during this process, sericin with a low-molecular-weight and narrow-molecular-weight distribution can be easily obtained upon subsequent hydrolysis of sericin by enzymes.

The scouring methods for silk yarn are generally divided into chemical scouring and enzymatic scouring, which are performed under alkaline conditions, and specifically include soap scouring, alkaline scouring, soap/alkali scouring, enzymatic scouring, and acid scouring.

The above soap scouring method usually is composed of first pretreating the silk fabric by immersing the silk fabric in a hot water bath at around 40° C. for 30 minutes, then scouring the silk fabric in a soap solution of 15% to 20% owf (on the weight of fiber) at 97° C. to 99° C. for about 2 hours and re-scouring according to the degree of scouring, then scouring with a sodium carbonate solution of 1% owf at 80° C. to 90° C. for 10 to 15 minutes, and finally treating with a sodium carbonate solution of 0.5% owf at 50° C. to 60° C., and then thoroughly washing.

The alkaline scouring method uses anhydrous sodium carbonate, sodium silicate, sodium metasilicate, sodium hydroxide, anhydrous sodium diphosphate, various condensed sodium phosphates, alkaline sodium, etc. as alkaline scouring agents, and immerses the raw silk in a 5% to 10% owf solution of anhydrous sodium carbonate at 40 to 50 times the amount of the sample, scours at 95° C. to 99° C. for 2 to 3 hours, re-scours according to the degree of scouring, and rinses sufficiently with a hot water bath at 40° C. to 50° C. for several times.

The soap/alkali scouring method above combines the benefits of soap scouring and alkali scouring and is the most common method of scouring using Marseille soap and alkaline sodium. The agents used include 4% to 8% by weight of soap, 1% by weight of sodium silicate, 1% by weight of nonionic surfactant, 1% by weight of hydrosulfide, 1% by weight of EDTA, and 0.5% by weight of tripolyphosphate, and are scoured at 95° C. to 98° C. in a bath ratio of 1:15 for about 2 hours, and re-scouring is performed according to the degree of twisting or scouring. After scouring, perform a single wash with a 0.5% to 1% by weight solution of sodium bicarbonate, followed by several thorough rinses with water at 50° C.

The enzymatic scouring is the application of proteolytic enzymes to the scouring of raw silk and is typically processed in three steps. First, as a pretreatment process, the raw silk is immersed in a solution of 0.03% by weight of soap and 0.015% by weight of sodium bicarbonate and treated at 90° C. to 95° C. for 15 minutes, and then washed with hot water at 40° C. to 60° C., and then, as an enzymatic treatment step, twice the amount of hydrosulfide of papain and 1 cc/1 of non-ionic activator are added to a 0.2% to 0.3% by weight solution of papain enzyme and treated at 75° C. to 80° C. for 1 to 2 hours, and then the raw silk is again immersed in a solution of 0.03% by weight of soap and 0.015% by weight of sodium bicarbonate and treated at 90° C. to 95° C. for 15 minutes, and then rinsed with warm water at 40° C. to 60° C. for several times to finish the scouring.

The above acid scouring method is a scouring method to change the touch and physical properties of silk by removing only a part of sericin without complete scouring and is divided into thirty percent scouring, fifty percent scouring, and seventy percent scouring, etc. The scouring agent used is Mcllvain's buffer solution (a mixture of 0.1 M citric acid and 0.2 M disodium hydrogen phosphate), which is adjusted to a pH of 2 to 12 and treated for 10 to 60 minutes to obtain the required scouring rate.

In the present disclosure, the step a) preferably applies a soap/alkali scouring method among the above-mentioned scouring methods. Specifically, the scouring can be performed by immersing the silk yarn in a scouring solution including: one or more alkaline agents selected from sodium carbonate, sodium bicarbonate, potassium carbonate, and sodium hydroxide; soap; one or more sulfates selected from sodium hyposulfite, calcium sulfate, and magnesium sulfate; and a solvent.

In this case, the scouring solution preferably has a concentration of alkali agent from 15% to 25% owf, soap from 5% to 15% owf, and sulfate is preferably added in a ratio of 0.01% to 5% owf.

In general, polymer electrolytes, such as proteins, increase their solubility in water when a suitable low concentration of salt is present, which is called salting-in. This phenomenon is due to the electrostatic interaction between the dissociation groups in the polymer electrolyte and the salt ions coexisting in the solution, and this can be used to relieve the aggregation of proteins that occurs during enzymatic hydrolysis.

In this case, multivalent anions can also be used as salts for salting-in, but sulfates are preferred, considering that the protein 0 is not denatured, the solubility of the salt is not affected by temperature, and the activity of the enzyme is not inhibited by the salt.

In the present disclosure, step a) above is preferably performed at 90° C. to 150° C. for 10 to 120 minutes, and more preferably at 110° C. to 130° C. for 10 to 60 minutes, since this increases the isolating efficiency of sericin while not affecting the physical properties of the fibroin fiber.

The step a) is not limited to processing equipment or the like, and as an example, the silk yarn and the scouring solution are placed in a chamber whose interior can be heated for high-temperature treatment, and the treatment is preferably performed under the conditions as described above. Furthermore, after the scouring is completed, the scouring solution is preferably passed through a filtration device such as an ultrafiltration membrane or filter paper to separate the solid and liquid. In this case, the sericin to be hydrolyzed is preferably soluble sericin rather than insoluble sericin.

In the present disclosure, step b) is obtaining low-molecular-weight sericin by mixing the enzyme composition with the separated soluble sericin solution and performing hydrolysis.

In the present disclosure, the enzyme composition is a proteolytic enzyme that can degrade sericin, which is basically a protein, and the proteolytic enzyme generally has substrate specificity, which only promotes a certain reaction of a certain substrate, and the factors affecting the action of the enzyme can be roughly divided into temperature and pH.

Like any chemical reaction, the reaction rate of an enzyme increases with increasing temperature, but since enzymes are made of proteins, the reaction rate decreases rapidly beyond the temperature at which denaturation begins, and enzymes eventually coagulate and lose their activity. The temperature at which the reaction rate is at its maximum is called the optimum temperature. Since enzymes are proteins, their properties are affected by pH. For example, when becoming extremely acidic or alkaline, the enzyme denatures and loses its activity completely.

Therefore, hydrolysis in the present disclosure is characterized by having sericin having a molecular weight of 3 kDa or less described above by optimizing conditions such as reaction temperature, reaction time, and reaction pH together with the enzyme used.

In general, proteases are categorized into endo-type proteases and exo-type aminopeptidases based on the method of protein degradation. Depending on the function of the amino acid present in the active site of the enzyme, the enzymes are also classified as serine protease, thiol (cysteine) protease, aspartyl protease, etc. Depending on the organism that produces the protease, proteases are divided into bacterial proteases and fungal proteases, and depending on the reaction condition, pH, proteases are also divided into acidic, neutral, and alkaline proteases, and each is known to have different specificities.

In the present disclosure, the enzyme is essentially hydrolyzing a high-molecular-weight sericin main chain to a low-molecular-weight, although several enzymes may be used, essentially any serine protease or subgroup thereof capable of accelerating the hydrolysis of peptide bonds.

Specifically, the serine protease may be subtilisin. The above subtilisins is a subgroup of serine proteases and includes, or is preferably composed of, I-S1 and I-S2 subgroups as defined in the literature [Siezen et al., Protein Eng. 4 (1991) 719-737], and [Siezen et al., Protein Science 6 (1997) 501-523]. Due to the highly conserved structure of the active site of serine proteases, subtilisin according to the present disclosure may be functionally equivalent to the proposed subgroup designated as subtilases by Siezen et al.

The subtilisins may include chemically or genetically modified mutants (protein engineered mutants) or derivatives and may have animal, plant or microbial origin. Examples of such subtilisins are derived from *Bacillus*, such as subtilisin Novo, subtilisin Carlsberg, subtilisin BPN', subtilisin 309, subtilisin 147, and subtilisin 168 (described in WO No. 89/06279), and the protease PD138 (described in WO No. 93/18140), further described in WO No. 98/020115, WO No. 01/44452, WO No. 01/58275, WO No. 01/58276, WO No. 03/006602, and WO No. 04/099401. Other examples include mixtures of mutants and proteases described in WO No. 92/19729, WO No. 98/20115, WO No. 98/20116, WO No. 98/34946, and WO No. 2011/036263.

Examples of commercially available subtilisins include Kannase™, Everlase™, Relase™, ESPERASE™, ALCALASE™, Durazym™, Savinase™, Ovozyme™, Liquanase™, Coronase™, Polarzyme™, Pyrase™, Pancreatic Trypsin NOVO: PTN), Bio-Feed™ Pro and Clear-Lens™ Pro; Blaze (all are commercially available from Novozymes A/S, Backsbærds, Denmark). Other commercially available subtilisins may include Ronozyme™ Pro, Maxatase™, Maxacal™, Maxapem™, Opticlean™, Properase™, Purafast™, Purafect™, Purafect Ox™, Purafact Prime™, Excellase™, FN2™, FN3™, and FN4™ (all commercially available from Genencor International Inc., Other examples include Primase™ and Gist-Brocades, BASF, or DSM). Duralase™, Blap R, Blap S, and Blap X (all commercially available from Henkel).

The subtilisin is preferably added in an amount of 1 part by weight or more with respect to 100 parts by weight of said soluble sericin or in a ratio of 1 to 30 parts by weight with respect to 100 parts by weight of the composition. In the case of an enzyme such as subtilisin, since the hydrolysis effect increases in a concentration-dependent manner, the amount added as described above is preferably more than 1 part by weight, and when less than 1 part by weight is added, the hydrolysis effect described above may be insufficient.

In addition, the enzyme composition may further include a second enzyme in addition to the subtilisin described above to further enhance the hydrolytic effect. Examples of such enzymes include lipases, cutinases, amylases, carbohydrases, cellulases, pectinases, pectate lyases, mannanases, arabinases, galactanases, xylanases, oxidases, laccases, and peroxidases, which may be used alone or in mixtures of two or more.

In the present disclosure, in the step b), the liquid soluble sericin and the enzyme composition are introduced into the reactor, and the temperature of the reactor, the pH of the composition, and the reaction time are adjusted to keep the enzyme active. Therefore, it is recommended to first adjust the internal temperature of the reactor to 30° C. and the pH to around 7 before adding the sericin and enzyme composition and proceeding with the reaction.

Specifically, the step b) depends on the type of enzyme, but preferably the pH is in a range of 5 to 9, more preferably in a range of 7 to 9, and the temperature is in a range of 30° C. to 70° C., more preferably in a range of 55° C. to 65° C. Furthermore, the reaction time is preferably from 1 to 24 hours, more preferably from 1.5 to 2.5 hours, allowing the activity of the enzyme to be controlled.

The present disclosure may include low-molecular-weight sericin prepared by the above preparing method and a cosmetic composition containing the low-molecular-weight sericin. At this time, the low-molecular-weight sericin has a molecular weight of 3 kDa or less. As a result, sericin is highly miscible with other cosmetic ingredients due to its good solubility in solvents, and additionally, the sericin can be well absorbed into the skin due to their low-molecular-weight.

In the present disclosure, the cosmetic composition may further include various additives in addition to sericin within a range that does not impair the purpose. Examples of such additives include polysaccharide polymers, essential oil components, humectants, thickeners, plant extracts, solvents, and the like.

The polysaccharide polymer maintains the viscosity of the composition similar to a thickener and particularly has the effect of increasing the solubility of sericin. Xanthan gum, one of the representative polysaccharide polymers, is a water-soluble polymer that is extracted from glucose or corn syrup. Xanthan gum has excellent heat and acid resistance, and while common thickeners decrease in viscosity in the presence of acids or alkalis, xanthan gum shows little change in viscosity with pH.

In addition to the above xanthan gum, polysaccharide polymers such as cellulose gum and alginic acid may be used. As such, the polysaccharide polymer of the present disclosure can be used very usefully in preparing an o/w type emulsion formulation because the polysaccharide polymer can adjust the viscosity of the formulation simultaneously with the dissolution of the polymeric sericin.

Specifically, the polysaccharide polymer used in the present disclosure may be at least one selected from the group consisting of gum, alginic acid, sodium alginate, calcium alginate, starch, agar carrageenan, cellulose-based polymer, gellan, pectin, dextran, glucan, glucomannan, Arabino Galactan, Furcelleran, Pullulan, Glucosamine and gelatin, but is not limited thereto.

The gums listed above include Xanthan gum, dehydroxanthan gum, cellulose gum, hydrolyzed cellulose gum, Carrageenan gum, Guar gum, *Styrax benzoin* gum, *Sclerotium* gum, biosaccharide gum, Arabic gum, Locust bean gum, Tamarind gum, Ghati gum, *Ceratonia siliqua* gum, *Astragalus gummifer* gum, hydrolyzed Rhizobian gum, and *Sclerotium* gum, but are not limited thereto.

The cellulose-based polymers include calcium carboxymethyl cellulose, carboxymethyl cellulose acetate butyrate, carboxymethyl cellulose acetate butyrate, carboxymethyl hydroxyethylcellulose, cellulose acetate, cellulose acetate butyrate, cellulose acetate butyrate, cellulose acetate propionate, cellulose acetate propionate carboxylate, cellulose acetate propionate carboxylate, cellulose succinate, cetyl hydroxyethylcellulose, ethylcellulose, hydroxybutyl methylcellulose, hydroxybutyl methylcellulose, hydroxyethylcellulose, hydroxyethyl ethylcellulose, hydroxypropylcellulose, hydroxypropyl methylcellulose, methylcellulose, hydroxypropyl methylcellulose acetate/succinate, methylcellulose, methyl ethylcellulose, methyl hydroxyethylcellulose, microcrystalline cellulose, potassium cellulose succinate, sodium cellulose succinate, and sodium cellulose sulfate, but are not limited thereto.

In the present disclosure, the essential oil component contains polyphenols and vitamin C as active ingredients and serves to amplify the effects of the sericin, such as antioxidation, whitening, and wrinkle improvement.

Examples of these essential oils include Eucalypus, Peppermint, Grapefruit, Nenolri, Niaouli, Lavender, Lime, Lemon, Lemongrass, *Melissa officinalis*, Rosemary, Rosewood, Marjoram, *Citrus madurensis*, Myrtle, Myrrh, Basil, *Verbena*, Birch, Bergamot, Bay, Benzoinum, Cypress, Sandalwood, Cinnamon, Cedarwood, Citronella, Orange sweet, Ylang ylang, Jasmine, Geranium, Juniper berry, Ginger, Chamomile, Camphor, Clary sage, Thyme, Tangerine, Tea tree, Palmarosa, Patchouli, Petitgrain, Franincense, Fennel, Hyssop, Green tea, Ginger, Chinese liquorice, Schisandra, Coptis, Aloe vera, Broccoli, and Citrus, which may be used alone or in a mixture of two or more.

The humectant is not limited to the type as long as it is conventionally added when preparing a cosmetic composition in the art. Examples of the above humectants may include at least one selected from the group consisting of dipropylene glycol (D. P. G), propylene glycol, dipropylene glycol, butylene glycol, 1,2-hexanediol, glycerine, betaine, glycereth-26, sorbitol, hexylene glycol, diglycerin, and panthenol, and a mixture of dipropylene glycol, butylene glycol, 1,2-hexanediol, betaine, panthenol, glycerin, and the like is preferably used.

The thickener is added to maintain the viscosity of the composition similarly to the polysaccharide polymer, and is not limited to the type as long as the thickener is commonly added in the art. Examples of the thickener include carbomers such as Carbopol 340, 940, 941, and 980, cellulose, hydroxyethyl cellulose, and sodium polyacrylate, among which carbomers are preferably used.

In the present disclosure, the solvent may be clean water, purified water, hard water, soft water, natural water, ocean deep water, electrolyzed alkaline ionized water, electrolyzed acidic ionized water, ionized water, and cluster water, and a mixture of one or more thereof may be used.

In addition to the above ingredients, the cosmetic composition, according to the present disclosure, may be supplemented with various other ingredients conventionally added in the art. Essential oils, such as jojoba esters; conditioning agents, such as ethylhexylglycerin, sodium hyaluronate, alginine, caprylyl glycol, biosaccharide gum-4, menadione, bioflavonoids; surfactants; chelating agents, such as disodium EDTA; emulsifiers such as dipotassium glycyrrhizate, polyglyceryl-10 laurate, polyglyceryl-10 myristate, caprylic/capric triglyceride, polyglyceryl-10 diisostearate, hydrogenated lecithin; colors; preservatives; flavors; and the like, which may be added in any number of types and amounts depending on the use, formulation, etc., of the composition.

In the present disclosure, the cosmetic composition is not limited to its formulation. For example, the above composition may include any one or more formulations selected from soft cosmetics, nutritional cosmetics, milk lotion, nutritional cream, massage cream, essence, eye cream, cleansing cream, cleansing foam, cleansing water, pack, spray, and powder.

Further, the cosmetic composition may have the form of a mask pack among the plurality of formulations. These can be prepared by immersing a commonly used sheet of water-stretchable film or non-woven fabric into the cosmetic composition, then taking it out and packaging the sheet.

Low-molecular-weight sericin, according to the present disclosure, can enhance absorption efficiency when applied to the skin and, especially, has excellent antioxidant and tyrosinase inhibitory effects, and thus can fundamentally inhibit the degradation of elastin and collagen, which maintain skin elasticity.

In addition, sericin has all essential amino acids except for tryptophan and thus can even be effectively used in wound dressings or food, in addition to cosmetic products.

Hereinafter, the present disclosure will be described in more detail with reference to examples. However, the following examples are only one example for explaining a preferred embodiment of the present disclosure, and the present disclosure is not limited to the following examples.

The physical properties of the specimens prepared through Examples were measured as follows.

(Molecular Weight of Sericin)

Polyacrylamide gel electrophoresis (SDS-PAGE) was used to confirm the molecular weight distribution of the extracted sericin protein. In order to prepare 2% (w/v) of silk sericin as a stock solution, 25 ml of D/W (1:50) was added to 0.5 g of freeze-dried powder sericin for each extraction and dissolved at 70° C. for 30 minutes. Thereafter, the supernatant, excluding insoluble was recovered sericin, by centrifugation at 3,000 rpm for 20 min to quantify the concentration for each sericin, and an equal amount of sericin (100 μg) was loaded onto Tris-Tricine SDS-PAGE (polyacrylamide gel electrophoresis) to determine the overall molecular weight distribution of sericin for each extraction.

Preparation Example 1

The molecular weight and concentration of sericin protein were measured in order to set the optimal extraction conditions for silk sericin extracted at high temperature and high pressure from silk yarn for each temperature and time. Four extraction conditions were performed: 2 hours and 6 hours at 95° C. and 30 minutes and 4 hours at 120° C. 0.5 g freeze-dried powder of sericin extract for each condition was stirred with 1:50 bath water at 70° C. for 1 hour to dissolve as much as possible and then centrifuged at 3,000 rpm for 20 minutes to recover the supernatant excluding insoluble sericin, and the concentration for each sericin was quantified. For the quantitative method, protein concentration was measured using Pierce BCA Protein Assay kit (ThermoFisher scientific), and the pH of sericin solution was measured using SevenEasy pH meter (Mettler Toledo), and the results are shown in Table 1.

TABLE 1

| Extraction conditions | Dissolving ratio | Concentration (mg/mL) | Total Concentration (g/L) | pH |
|---|---|---|---|---|
| 95° C., 2 h | 1:50 | 19.09 | 19.08 | 5.7 |
| 95° C., 6 h | 1:50 | 22.91 | 22.88 | 5.7 |
| 120° C., 30 min | 1:50 | 21.92 | 21.92 | 6.3 |
| 120° C., 4 h | 1:50 | 22.06 | 22.04 | 5.6 |

As shown in Table 1 above, the recovery of sericin by extraction condition shows the highest recovery of 22.88 g/l and 22.04 g/l when extracted at 95° C. for 6 hours and 120° C. for 4 hours, respectively, but there is no significant difference with sericin (21.92 g/l) extracted at 120° C. for 30 minutes. In addition, the intrinsic pH of sericin for each extraction condition was maintained in the range of 5.6 to 6.3. Through this, it is concluded that the optimal sericin extraction condition for securing raw materials is to recover sericin at 120° C. for 30 min, which is the most suitable in terms of energy saving and time-saving.

Figure 1B:
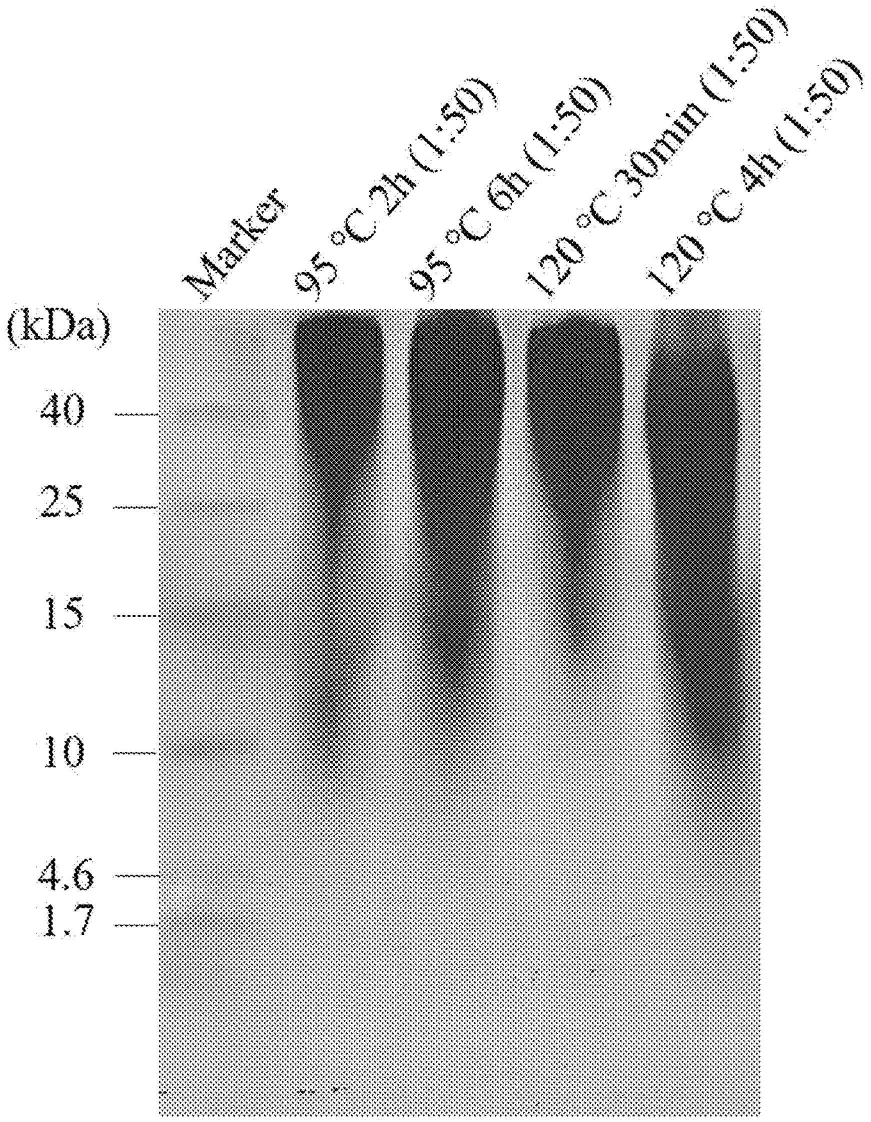

FIGS. 1A and 1B show the molecular weight distribution of sericin by extraction conditions, and the molecular weight distribution on SDS-PAGE shows that the sericin protein is characterized by protein thermal denaturation due to high temperature and pressure rather than inherent bands. The molecular weight distribution shows a low-molecular-weight due to thermal hydrolysis in the order of 4 hours at 120° C., 6 hours at 95° C., 30 minutes at 120° C., and 2 hours at 95° C. In addition, most of the sericin was present in the 10 to 245 kDa phase under high temperature and high pressure extraction conditions.

Figure 2A:
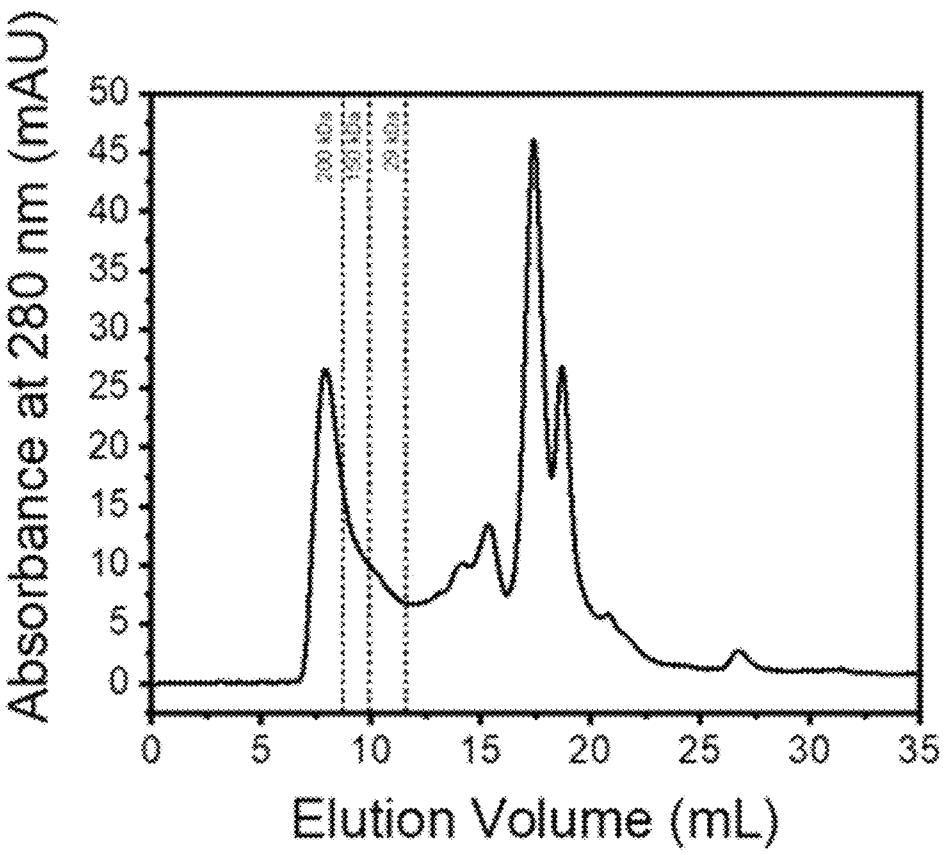
FIG. 2A shows the molecular weight distribution of the scoured sericin prepared through Preparation Example 1.
Figure 2B:
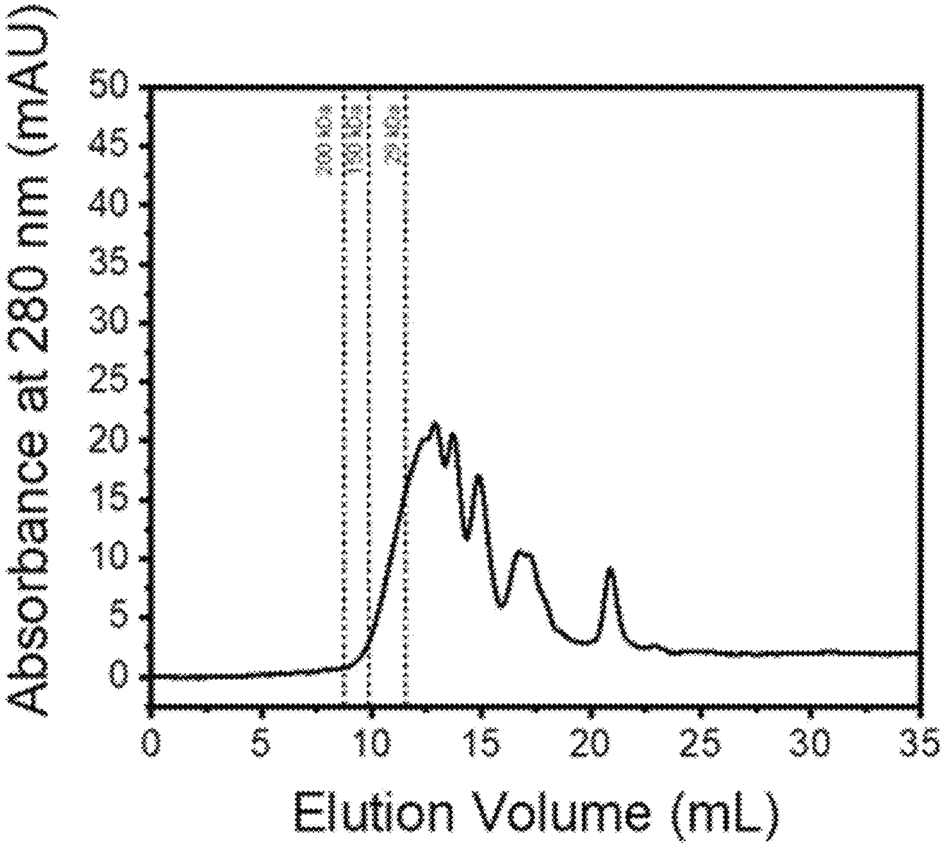
FIG. 2B shows the molecular weight distribution of commercially available sericin.

FIGS. 2A and 2B show the molecular weight of sericin scoured at 120° C., 4 hours, and the molecular weight distribution of commercially available sericin (China) analyzed at an absorbance intensity of 280 nm. As shown in FIG. 2A, the sericin scoured according to the present disclosure contains a large content of sericin with a molecular weight of 200 kDa or more, but most of the sericin has a low-molecular-weight of 10 kDa or less. In contrast, the commercial sericin in FIG. 2B had a high content of sericin with a molecular weight of 30 kDa or less, but compared to the scoured sericin of the present disclosure, the amount of sericin with a low-molecular-weight of 10 kDa or less was small.

Preparation Example 2

To confirm the degree of hydrolysis of sericin according to the kinds of enzyme, a total of 7 kinds of endopeptidase type ALCALASE™, ESPERASE™, protamax, bromelain, papain, neutrase and exopeptidase type flavourzyme were prepared. At this time, sericin extracted from the sericin prepared in Preparation Example 1 at 120° C. for 30 minutes was used as a substrate sample, and after centrifugation, insoluble sericin was removed and soluble sericin was used.

The enzymes were used as single enzymes (ALCALASE™, flavorzyme, ESPERASE™, protamax, bromelain, papain, neutrase) or as two-enzyme mixtures (ALCALASE™ and flavorzyme; ESPERASE™ and flavorzyme; protamax and flavorzyme; bromelain and flavourzyme; papain and flavourzyme; neutrase and flavourzyme;), and the combination of a two-enzyme mixture composed of a combination of endopeptidase and exopeptidase hydrolases.

The reactants after hydrolysis were subjected to enzyme inactivation at 85° C. for 10 min, and then the supernatant was collected by centrifugation (10,000 rpm, 10 min). After diluting the supernatant 20 times with D/W, the absorbance value measured at 271 nm, which is the maximum absorption wavelength of sericin, with a spectrophotometer (UV/VIS Nano Spectrophotometer, Nabi, Microdigital) was used as a measure of solubility.

Example 1

In order to minimize the change in pH during the enzyme reaction of Preparation Example 2, the pH was adjusted using 1 M acetic acid and an average of 26.5% ammonia hydroxide. 1 mg of soluble sericin was treated with 0.1 mg of an enzyme (10% of sericin concentration), and the enzyme was inactivated by hydrolysis at a temperature of 50° C. and pH (4, 5, 6, 7, 8, 9) for 8 hours, and then the supernatant was collected to measure the absorbance with pH change.

Figure 3A:
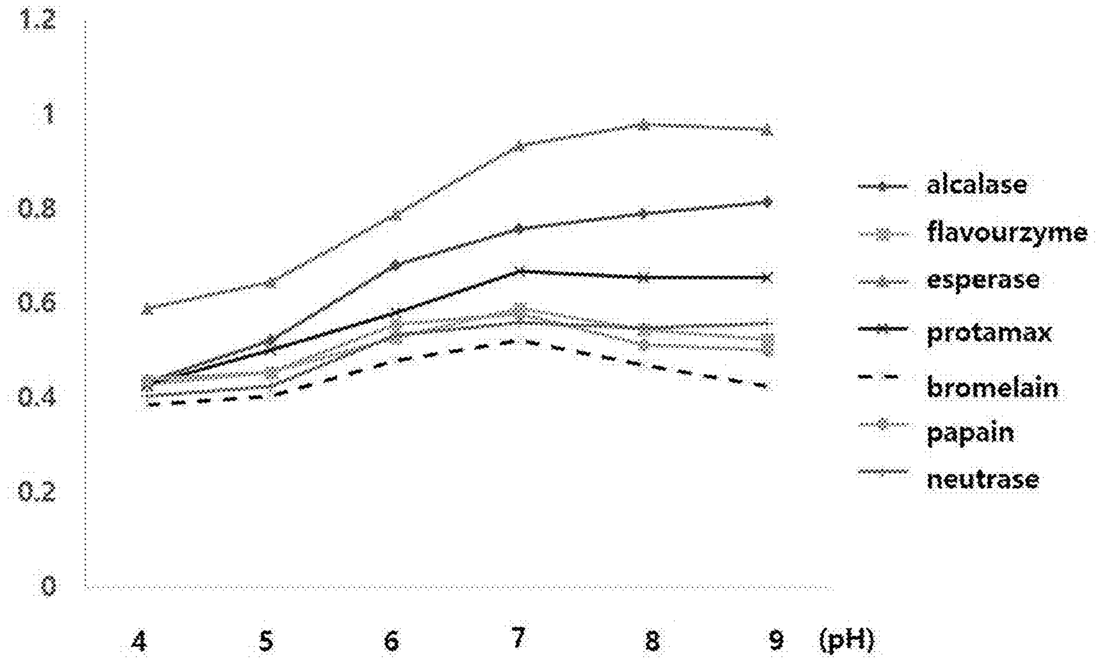
FIGS. 3A and 3B show the hydrolytic activity of sericin for each pH according to Example 1.
Figure 3B:
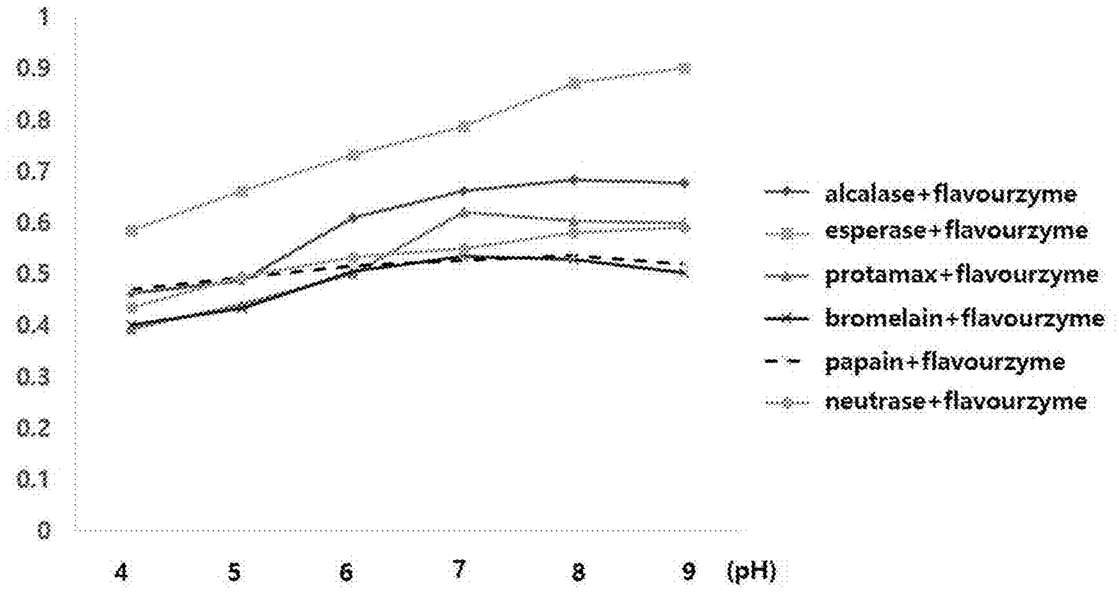

Referring to FIGS. 3A and 3B, in the case of single enzymes, ALCALASE™, ESPERASE™, protamax, and neutrase two-enzyme mixtures showed high activity around pH 7 to 9 and flavourzyme, papain, and bromelain showed high activity around pH 6 to 8. In the case of two-enzyme mixtures, ALCALASE™ and flavourzyme; neutrase and flavourzyme; papain and flavourzyme; and bromelain and flavourzyme; ESPERASE™ and flavourzyme showed high activity around pH 6 to 9; and protamax and flavourzyme; showed high activity around pH 7 to 9. Among them, ESPERASE™ andALCALASE™ showed the highest activity as single enzymes, and two-enzyme mixtures also showed high activity for the flavourzyme group containing a mixture of ESPERASE™ and ALCALASE™.

However, the single enzyme was found to have slightly higher activity than the two-enzyme mixtures, which may be due to substrate competition between the two enzymes, resulting in reduced activity compared to the single enzyme. Overall, the enzymes with optimal activity were ALCALASE™ and ESPERASE™, which showed the highest activity in the pH range of 7 to 9.

Example 2

1 mg of soluble sericin from Preparation Example 2 was treated with 0.1 mg of an enzyme (10% of the sericin concentration), and the enzyme was inactivated by hydrolyzing for 8 hours at pH of 7 and temperature (30° C., 40° C., 50° C., 60° C., and 70° C.), respectively, and then the supernatant was collected to measure the absorbance with temperature change.

Figure 4A:
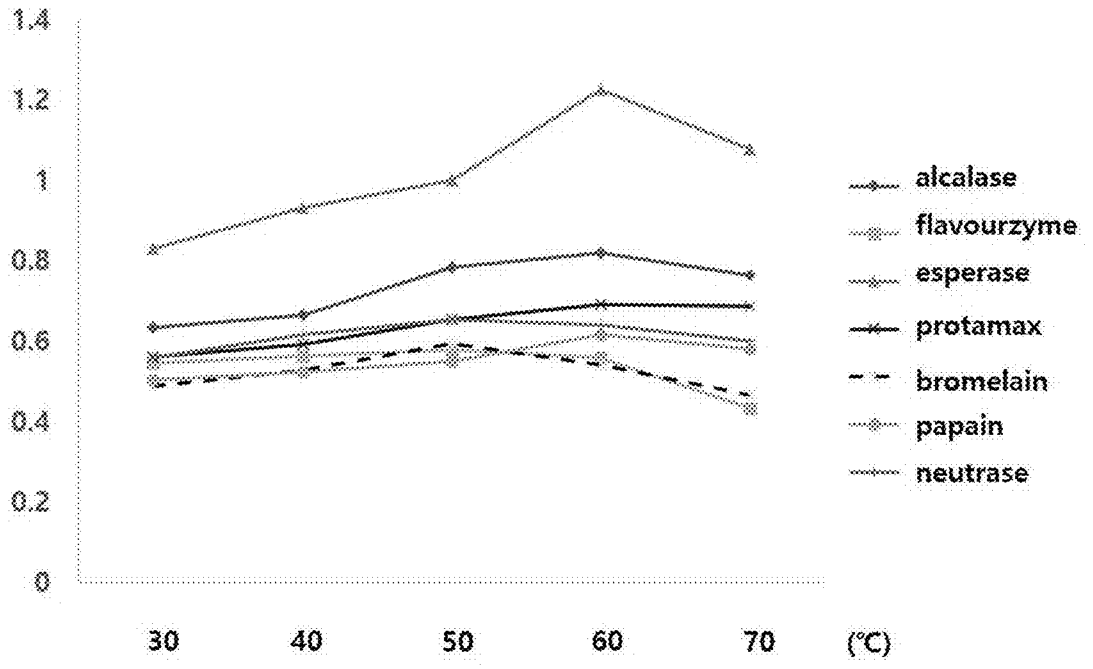
FIGS. 4A and 4B show the hydrolytic activity of sericin for each temperature change according to Example 2.
Figure 4B:
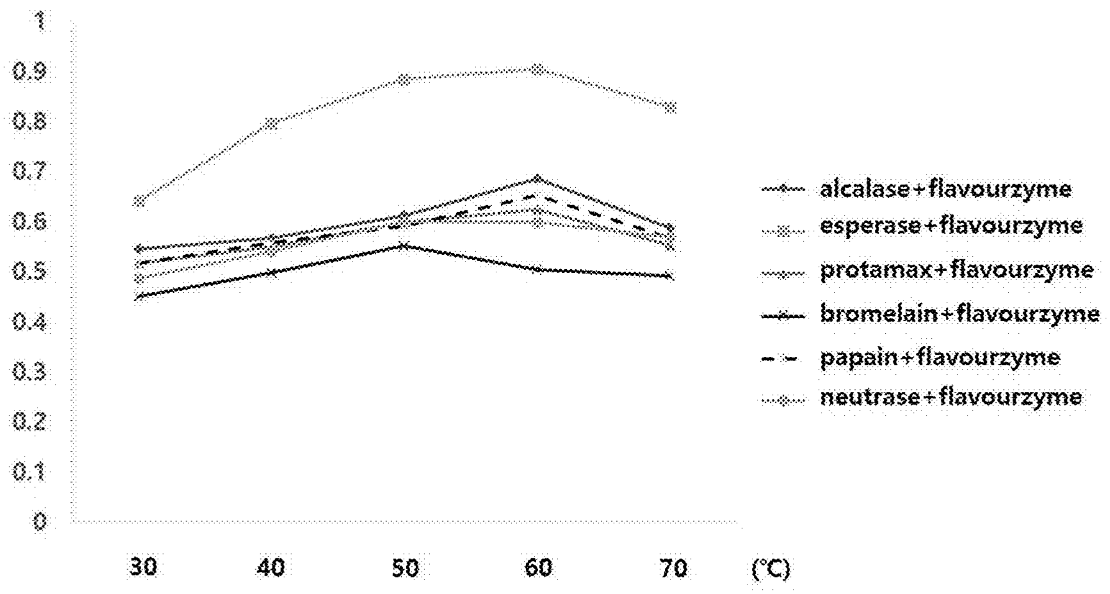

Referring to FIGS. 4A and 4B, in the case of single enzymes, ALCALASE™, ESPERASE™, protamax, and papain showed high activity at 60° C., while flavourzyme, bromelain, and neutrase showed high activity at 50° C. In the case of two-enzyme mixtures, ALCALASE™ and flavourzyme; ESPERASE™ and flavourzyme; protamax and flavourzyme; papain and flavourzyme showed high activity at 60° C., and bromelain and flavourzyme; neutrase and flavourzyme showed high activity at 50° C.

In addition, in the case of enzymatic activity according to temperature change, the hydrolysis activity is somewhat higher for a single enzyme than for two-enzyme mixtures, and ESPERASE™ and ALCALASE™ were identified as the optimal enzymes for low-molecular-weight sericin according to temperature change.

Example 3

1 mg of soluble sericin from Preparation Example 2 was treated with 0.1 mg of an enzyme (10% of the sericin concentration), the pH was fixed at 7 and the temperature was adjusted to the optimum temperature for each enzyme identified in Example 3, and hydrolyzed by time (1, 2, 3, 4, 8, 12, 18, 24 hours) to measure the absorbance according to the time change.

Figure 5A:
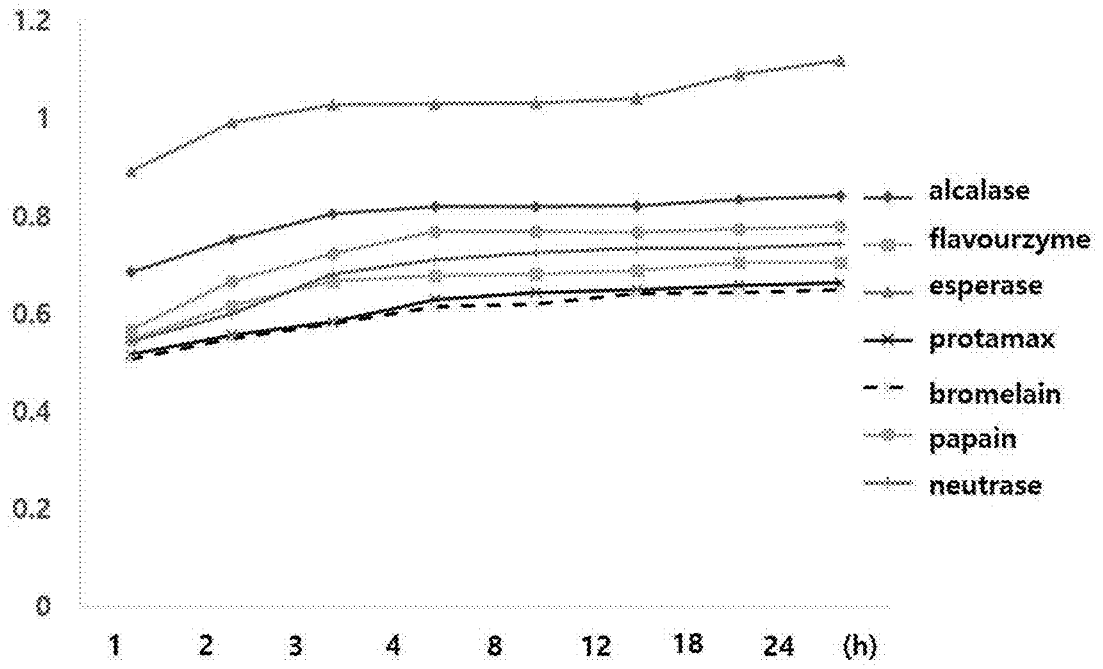
FIGS. 5A and 5B the hydrolysis activity of sericin according to the hydrolysis time according to Example 3.
Figure 5B:
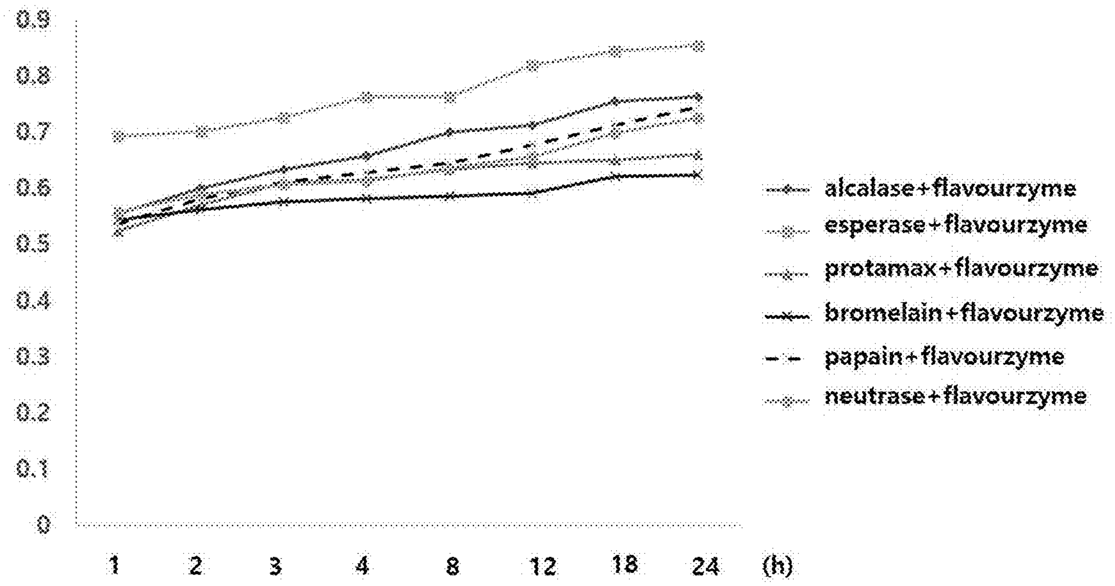

Referring to FIGS. 5A and 5B, in the case of single enzymes, each enzyme showed a rapid increase in hydrolytic activity up to 2 hours after initial treatment, followed by a moderate increase in hydrolytic activity from 2 to 24 hours. In the case of two-enzyme mixtures, most of them show a continuous increase in hydrolytic activity for up to 24 hours, except for protamax and flavourzyme; bromelain and flavourzyme. In the case of single enzymes, most of them show significant hydrolytic activity of sericin up to 2 hours, followed by moderate hydrolytic activity for up to 24 hours.

On the other hand, the two-enzymes continue to have hydrolytic activity up to 24 hours, which is thought to be due to substrate competition between the two-enzymes, resulting in a somewhat delayed reaction time compared to the single enzymes, where most of the hydrolytic activity occurs at the beginning of the reaction. The enzymatic hydrolysis activity over time showed that ESPERASE™ and ESPERASE™+flavourzyme had the highest enzymatic activity, followed by ALCALASE™ and ALCALASE™+flavourzyme, and the optimal reaction time was determined to be 4 to 12 hours.

Example 4

1 mg of soluble sericin from Preparation Example 2 was mixed with the enzymes but adjusted to 1%, 2.5%, 5%, 10%, 20%, and 30% of the sericin concentration for each enzyme, and the pH was fixed at 7, but the temperature was adjusted to the optimum temperature for each enzyme identified in Example 3. The enzymes were inactivated by hydrolysis for 8 hours, and then the supernatant was collected to measure the absorbance with the change of enzyme concentration.

Figure 6A:
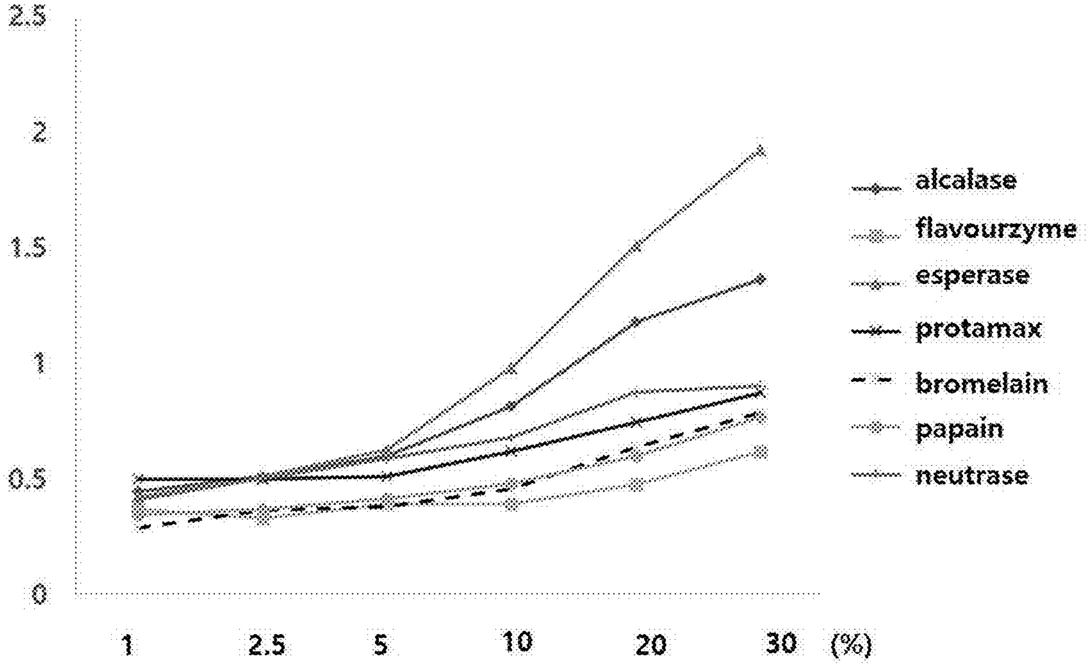
FIGS. 6A and 6B show the hydrolytic activity of sericin for each enzyme concentration according to Example 4.
Figure 6B:
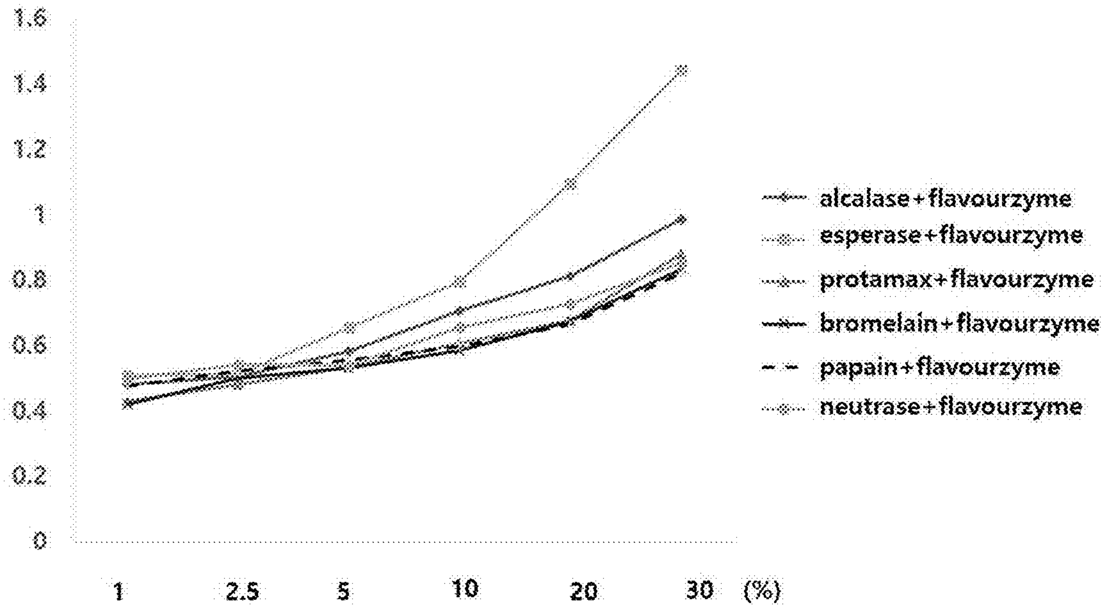
Figure 7A:
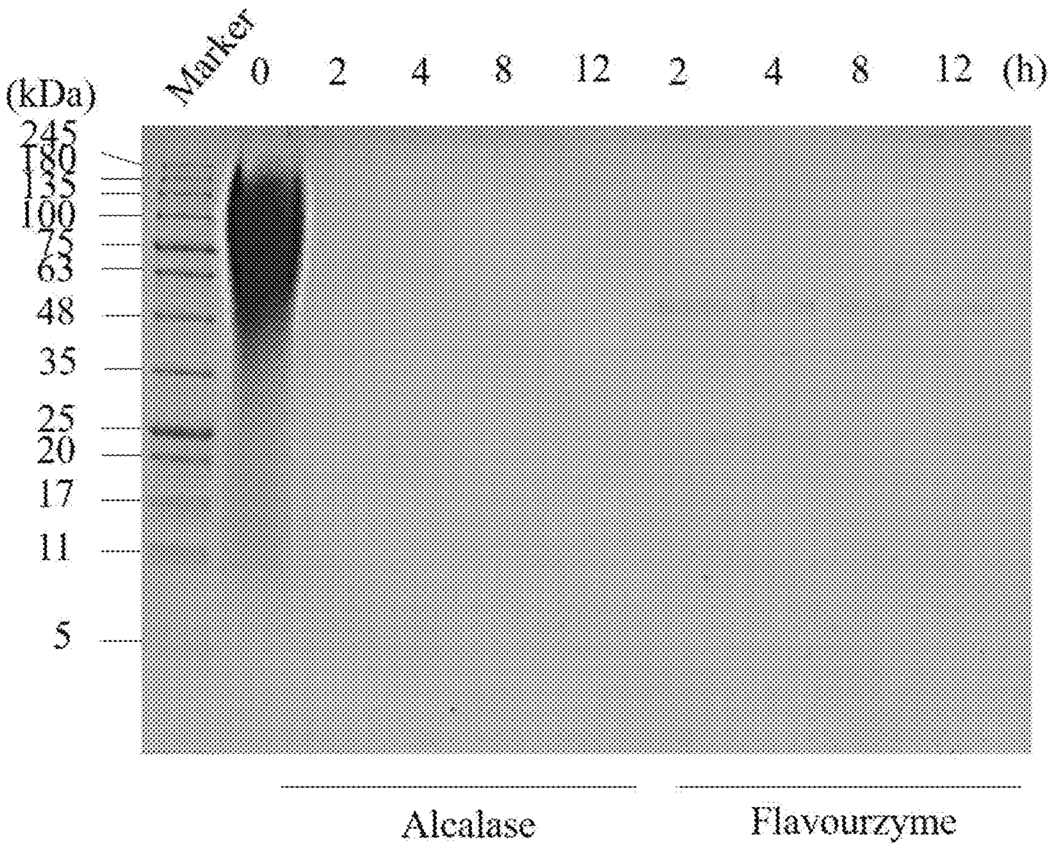
Figure 7B:
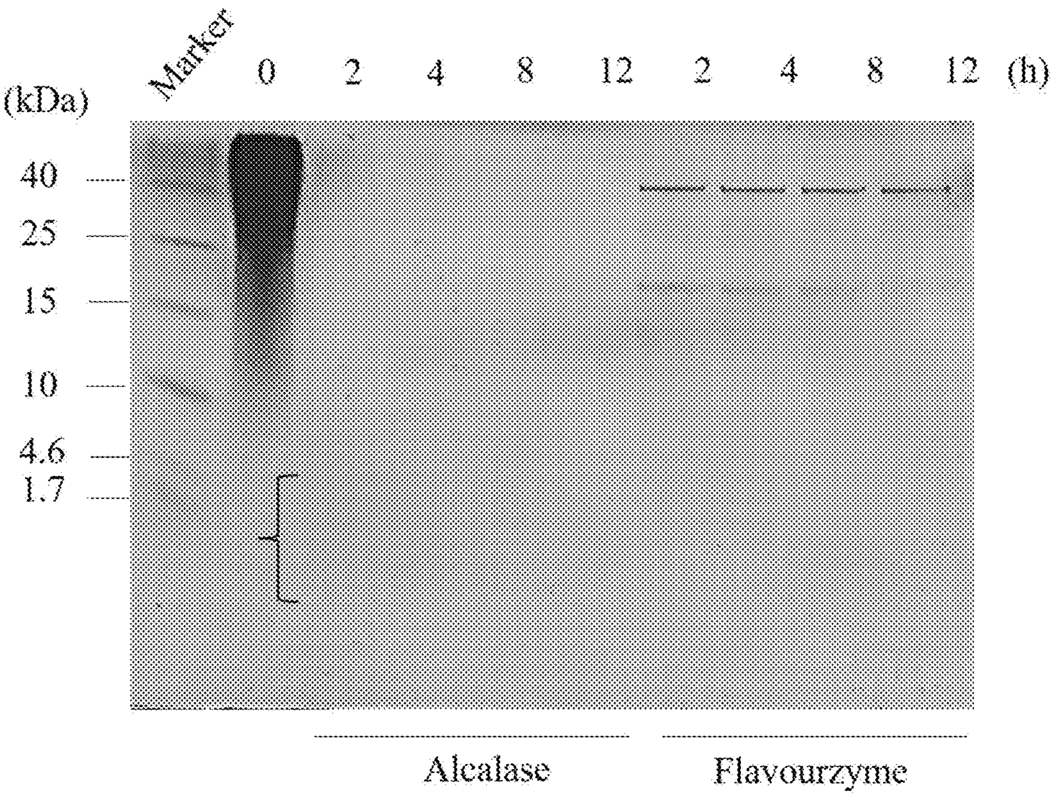
Figure 8A:
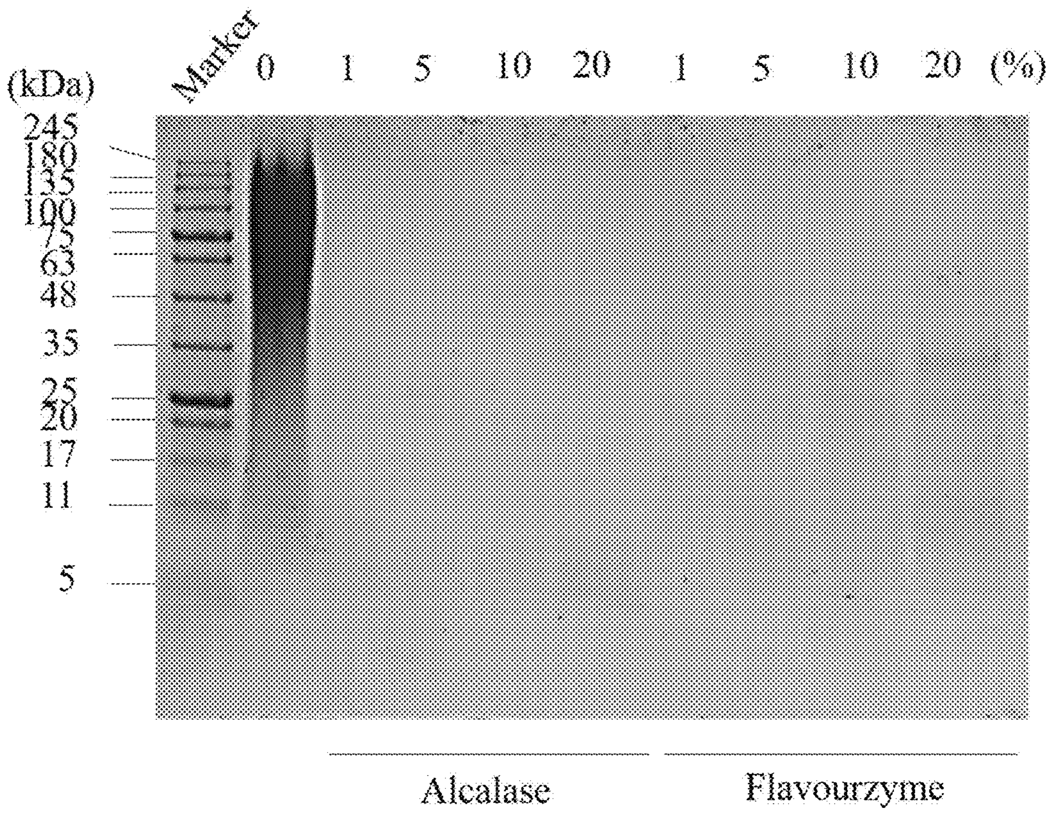
Figure 8B:
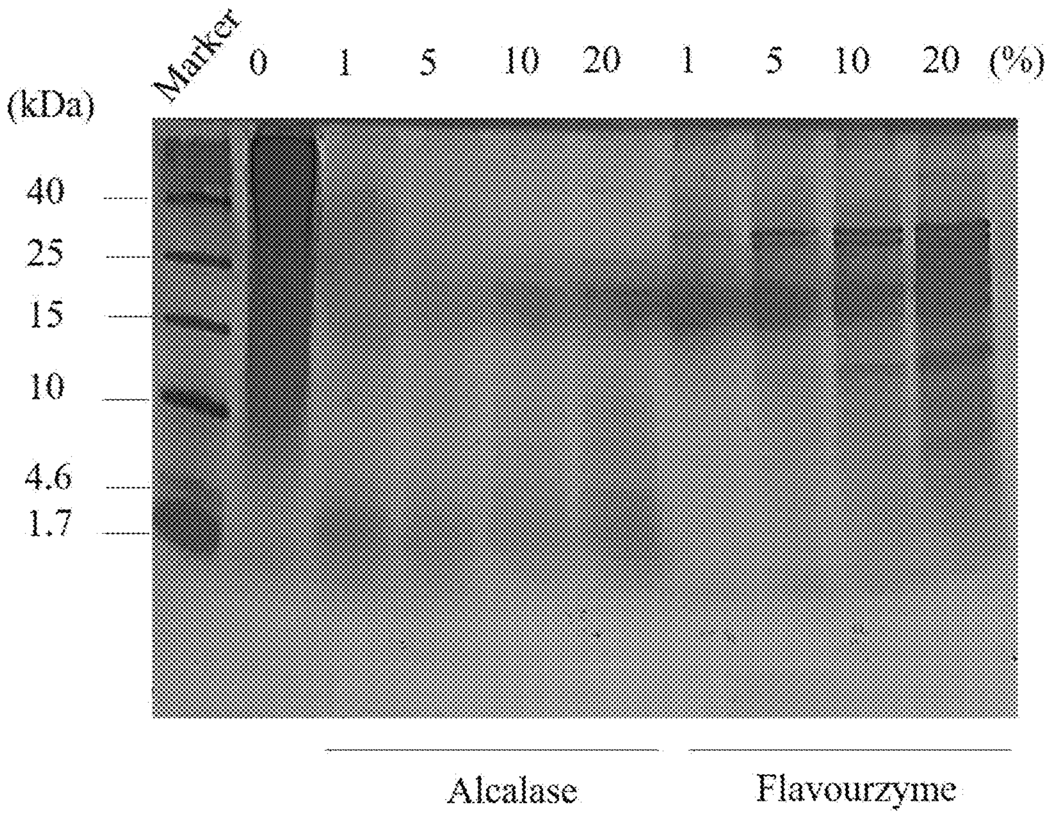

Referring to FIGS. 6A and 6B, in the case of single enzymes, all enzymes show a gradual increase in activity in a concentration-dependent manner from 1% concentration onwards, while ESPERASE™ and ALCALASE™ show a sharper increase in activity at 10% concentration. This seems to be related to the thermal stability of the protein, and while the activity of proteins tends to decrease in prolonged reactions, ESPERASE™ and ALCALASE™ are considered to be more thermally stable than other enzymes, even in prolonged reactions. In the case of the two-enzyme mixture, like in the case of the single enzyme, the enzyme concentration gradually increases in a concentration-dependent manner from 1% onward, particularly the ESPERASE™+ flavorzyme, which shows a more rapid increase in activity from 10% onward. In terms of hydrolysis activity by enzyme concentration, the single-enzyme treatment was judged to have higher hydrolysis activity than the two-enzyme mixture treatment.

Example 5

First, the pH of the sericin solution was adjusted using 1 M acetic acid and an average of 26.5% ammonia hydroxide to minimize changes in pH during the enzymatic reaction. Then mix each enzyme in 1 mg of the soluble sericin of Preparation Example 2, but set the temperature of the composition after addition as follows: the temperature of ALCALASE™, ESPERASE™, protamax, papain is 60° C.; the temperature of flavourzyme, bromelain, neutrase was 50° C.; the temperature of ALCALASE™+flavourzyme, ESPERASE™+flavourzyme, protamax+flavourzyme, papain+flavourzyme was 60° C.; and the temperature of bromelain+flavourzyme, neutrase+flavourzyme was 50° C. In addition, the addition amount was 0.05 mg, and when two types of enzymes were mixed, they were mixed at a ratio of 1:1.

High-molecular-weight and low-molecular-weight sericin were identified on SDS-PAGE by hydrolysis at pH of 6, 7, 8, and 9 and time of 2, 4, 8, and 12 hours. Specifically, to determine the high-molecular-weight sericin hydrolysis pattern, each sample was diluted with an equal volume of 2×Laemmli sample buffer and heat treated at 95° C. for 5 minutes. Each protein sample (250 μg/50 μl) was loaded into each well of a Tris-Glycine SDS-PAGE gel and electrophoresed at 120 V for 1 hour. After electrophoresis, the gel was stained with a staining solution for 1 hour, and then the gel was decolorized with decolorizing solution, and the sericin protein hydrolysis pattern was observed and photographed on an LED light pad. To determine the pattern of low-molecular-weight sericin hydrolysis, each sample was diluted with an equal volume of Tricine sample buffer and heat treated at 95° C. for 5 minutes. Each protein sample (150 μg/30 μl) was loaded into each well of a Tris-Tlycine SDS-PAGE gel and electrophoresed at 100 V for 1.5 hours. After electrophoresis, the proteins were fixed in fixative solution (40% methanol, 10% acetic acid) for 30 minutes and stained in staining solution (0.025% Coomassie Blue G-250, 10% acetic acid) for 1 hour, followed by three times of destaining with 15-minute increments in destaining solution (10% acetic acid), and the low-molecular-weight peptide pattern of the sericin protein was observed and photographed on an LED light pad.

TABLE 2

| | | Molecular weight range by pH (kDa) | | | |
|---|---|---|---|---|---|
| Enzyme | Electrophoresis | 6 | 7 | 8 | 9 |
| alclase | A | 5 | 5 | 5 | 5 |
| | B | <1.7~4.6 | <1.7~4.6 | <1.7 | <1.7~4.6 |
| flavourzyme | A | 5~48 | 5~48 | 5~48 | 5~48 |
| | B | 4.6~40 | 4.6~40 | 10~40 | 4.6~40 |
| esperase | A | 5 | 5 | 5 | 5 |
| | B | <1.7~4.6 | <1.7~4.6 | <1.7~>4.6 | 1.7~25 |
| protamax | A | 5~63 | 5~<63 | 5~63 | 5~<63 |
| | B | <1.7~>40 | <1.7~>40 | 1.7~>40 | 1.7~>40 |
| bromelain | A | 5~>100 | 5~100 | 5~100 | 5~100 |
| | B | 4.6~>40 | >1.7~>40 | 4.6~>40 | 4.6~>40 |
| papain | A | 5~<100 | 5~>40 | 5~25 | 5~25 |
| | B | 1.7~>40 | <1.7~>40 | 4.6~40 | 4.6~40 |
| neutrase | A | 5~63 | 5~<63 | 5~63 | <63 |
| | B | <1.7~>40 | 4.6~>40 | 4.6~>40 | 4.6~>40 |
| alcalase + | A | 5 | 5 | 5~35 | 5 |
| flavourzyme | B | <1.7~4.6, ≤40 | <1.7~4.6, ≤40 | <4.6, <40 | <1.7~4.6 |
| esperase + | A | 5 | 5 | 5 | 5 |
| flavourzyme | B | <1.7~4.6, ≥25 | <1.7~4.6, ≥25 | 1.7~4.6, ≥25 | <1.7~4.6, ≥25 |
| protamax + | A | 5~63 | <63 | 5~63 | 5~63 |
| flavourzyme | B | <4.6~>40 | 4.6~>40 | 4.6~>40 | 1.7~>40 |
| bromelain + | A | 5~>63 | 5~<63 | 5~>63 | 5~63 |
| flavourzyme | B | <4.6~>40 | >4.6~>40 | >10 | >4.6~40 |
| papain + | A | 5~>25 | 5~25 | 5~25 | 5~11 |
| flavourzyme | B | 4.6~25 | 4.6~25 | 4.6~25 | 4.6~<25 |
| neutrase + | A | 5~63 | <63 | 5~63 | 5~63 |
| flavourzyme | B | 4.6~>40 | 4.6~>40 | 4.6~40 | 4.6~40 |

In Table 2, A means Tris-Glycine SDS-PAGE, and B means Tris-Tricine SDS-PAGE.

In Table 2 above, Tris-Glycine SDS-PAGE gels are used to determine high-molecular-weight molecules between 5 and 100 kDa, and Tris-Tricine SDS-PAGE gels are used to visibly determine low-molecular-weight molecules in the range of 5 kDa or less to 40 kDa. As shown in Table 2 above, it can be seen that basically single enzymes are more efficient than mixed enzymes, and among the single enzymes, ALCALASE™ and ESPERASE™ are hydrolyzed to the smallest size and have the smallest median molecular weight range. Other enzymes were confirmed to have slightly lower hydrolytic activity than the above enzymes.

Example 6

In Example 5 below, the molecular weight of hydrolyzed sericin according to a single enzyme was determined when the pH was fixed at 6.3, and the enzymes were added at a ratio of 1%, 5%, 10%, and 20% of the weight of sericin per enzyme. In particular, as the ratio of enzyme increased, hydrolysates clustered at a certain molecular weight, which suggests that the molecular weight of high molecules that are invisible on the SDS-PAGE is more actively degraded by the increase of enzyme and clustered at a certain low molecular weight, resulting in an increase in concentration.

TABLE 3

| | | Molecular weight range by concentration (kDa) | | | |
|---|---|---|---|---|---|
| Enzyme | Electrophoresis | 1 | 5 | 10 | 20 |
| alclase | B | <1.7~40 | <1.7~<25 | <1.7~<25 | <1.7~<25 |
| flavourzyme | B | >15 | >10 | >4.6 | 1.7~25 |
| esperase | B | 1.7~40 | <1.7~4.6 | <1.7~4.6 | <1.7~4.6 |
| protamax | B | 1.7~40 | 1.7~40 | 1.7~40 | 1.7~40 |
| bromelain | B | >4.6~40 | >4.6~25 | >4.6~25 | >4.6~25 |
| papain | B | 1.7~40 | 1.7~40 | 1.7~40 | 1.7~40 |
| neutrase | B | 1.7~>40 | 1.7~>40 | 1.7~>40 | 1.7~>40 |

In Table 3, B means Tris-Tricine SDS-PAGE.

As shown in Table 3, as the enzyme treatment concentration for sericin increases, all enzymes increase the concentration of low-molecular-weight sericin in a concentration-dependent manner. However, only two enzymes, ALCALASE™ and ESPERASE™, were found to degrade most of the high-molecular-weight sericin to form low-molecular-weight sericin with an average molecular weight of 3 kDa.

The embodiments that have been described herein above are merely illustrative of the technical idea of the present disclosure, and thus various modifications, changes, alterations, substitutions, subtractions, and additions may also be made by those skilled in the art without departing from the gist of the present disclosure. The embodiments disclosed in the present disclosure are not intended to limit the scope of the present disclosure, and the technical spirit of the present disclosure should not be construed as being limited to the embodiments. The protection scope of the present disclosure should be construed as defined in the following claims, and it is apparent that all technical ideas equivalent thereto falls within the scope of the present disclosure.

The invention claimed is:

1. A method of preparing low-molecular-weight silk sericin, the method comprising:

a) scouring a silk yarn with a scouring solution to separate the silk yarn into fibroin fibers and sericin; and b) mixing the separated sericin with an enzyme composition to prepare low-molecular-weight sericin, wherein the low-molecular-weight sericin has a molecular weight of 3 kDa or less, wherein the enzyme composition comprises a solvent, and a single enzyme selected from subtilisin or a derivative thereof, wherein the enzyme composition has a concentration of 1% to 30% by weight based on the weight of sericin per enzyme, wherein the enzyme composition has a pH in a range of 5 to 9, and wherein the step b) is performed at 30° C. to 70° C. for 1 to 24 hours.

2. The method of claim 1, wherein the step a) is performed at 90° C. to 150° C. for 10 to 120 minutes.

3. The method of claim 1, wherein the scouring solution comprises:

one or more of alkaline agents selected from the group consisting of sodium carbonate, sodium bicarbonate, potassium carbonate, and sodium hydroxide;

soap;

one or more sulfates selected from the group consisting of sodium hyposulfite, calcium sulfate, and magnesium sulfate; and a solvent.

4. The method of claim 1, wherein the enzyme composition has a concentration of 1% to 30% by weight and a pH in a range of 7 to 9.

5. The method of claim 1, wherein the step b) is performed at 60° C. to 70° C. for 1 to 24 hours.

6. The method of claim 1, wherein the step b) is performed at 55° C. to 65° C.

7. The method of claim 1, wherein the step b) is performed for 1.5 to 2.5 hours.

8. The method of claim 1, wherein the enzyme is present at a concentration of 1% to 20% by weight based on the weight of sericin per enzyme.

9. The method of claim 1, wherein the enzyme is present at a concentration of about 10% by weight based on the weight of sericin per enzyme.

10. The method of claim 1, wherein the enzyme composition comprising the single enzyme has higher activity, as compared to a two-enzyme system.

11. The method of claim 1, wherein the enzyme composition comprising the single enzyme has higher activity or higher hydrolysis activity, as compared to a two-enzyme system.

12. The method of claim 1, wherein the enzyme composition comprising the single enzyme has faster reaction time, as compared to a two-enzyme system.

13. The method of claim 1, wherein the enzyme composition comprising the single enzyme produces a product having a smaller median molecular weight range, as compared to a two-enzyme system.

* * * * *